United States Patent [19]
Wiechers et al.

[11] Patent Number: 5,300,284
[45] Date of Patent: Apr. 5, 1994

[54] GLYCOSAMINOGLYCANASE INHIBITOR ANDETHANE DIOL COMPOSITION FOR MAINTENANCE OF HAIR GROWTH

[75] Inventors: Johann W. Wiechers, Sharnbrook; Michael R. Lowry, Mickle Trafford; John Wollers, Bebington; Stuart K. Pratley, West Kirby, all of England

[73] Assignee: Chesebrough-Pond's USA Co., Division of Conopco, Inc., Greenwich, Conn.

[21] Appl. No.: 936,968

[22] Filed: Aug. 28, 1992

[30] Foreign Application Priority Data

Sep. 4, 1991 [GB] United Kingdom ............... 9118979

[51] Int. Cl.⁵ .......................... A61K 7/06; A61K 7/00
[52] U.S. Cl. ........................... 424/70; 424/401; 514/880
[58] Field of Search ............ 424/70, 401; 514/880, 514/881

[56] References Cited

U.S. PATENT DOCUMENTS

| | | | |
|---|---|---|---|
| 4,975,441 | 12/1990 | Gibson | 514/425 |
| 5,015,470 | 5/1991 | Gibson | 424/70 |
| 5,037,643 | 8/1991 | Green | 424/70 |
| 5,081,151 | 1/1992 | Davis et al. | 514/574 |
| 5,096,697 | 3/1992 | Adachi | 424/47 |
| 5,106,609 | 4/1992 | Bolich | 514/781 |
| 5,130,142 | 7/1992 | Wong | 514/880 |
| 5,185,325 | 2/1993 | Brawn et al. | 514/23 |

FOREIGN PATENT DOCUMENTS 2438534 2/1976 Fed. Rep. of Germany.

*Primary Examiner*—Thurman K. Page
*Assistant Examiner*—Sally Gardner
*Attorney, Agent, or Firm*—Milton L. Honig

[57] ABSTRACT

A composition for topical application to mammalian skin or hair is provided which comprises:
i) an effective amount of from 0.5 to 50% by weight of a glycosaminoglycanase inhibitor chosen from specific monosaccharide derivatives
ii) from 0.5 to 50% by weight of ethane diol; and
iii) up to 99% by weight of a cosmetically acceptable vehicle for the glycosaminoglycanase inhibitor.

15 Claims, No Drawings

GLYCOSAMINOGLYCANASE INHIBITOR AND ETHANE DIOL COMPOSITION FOR MAINTENANCE OF HAIR GROWTH

FIELD OF THE INVENTION

The invention relates to cosmetic and pharmaceutical compositions for topical application to mammalian skin or hair, containing a hair growth promoter which is capable of increasing or maintaining hair growth, especially terminal hair growth on the human scalp.

BACKGROUND TO THE INVENTION AND PRIOR ART

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

Also, as male pattern baldness proceeds, new hair growth, where it occurs, tends to be finer than before, this being due at least partly to a decrease in the average diameter of individual hair follicles. Although this phenomenon is seen as a very gradual development associated with ageing, it is most apparent when actual hair loss begins to occur, for example at the onset of male pattern baldness. At this stage, the decrease in the average diameter of individual hair follicles is more rapid.

The Promotion of Hair Growth

Within the last decade, an increasing number of proposals has appeared in the patent literature suggesting that substances can be applied topically to the skin, particularly to the scalp, in order to maintain, promote or increase hair growth in the human subject.

For example, the use of inhibitors of enzymes, particularly of glycosidases whose activity is believed to curtail the hair growth cycle, are advocated in order to reverse this process and so extend the hair growth cycle, maintaining it in particular in the anagen phase.

Examples of such inhibitors include glycosaminoglycanase inhibitors, as described by Unilever, such as aldonomonolactones and certain derivatives thereof in EP-A-277 428, and hexosaccharic acids and certain derivatives thereof in EP-A-375 388.

A composition for topical use by the consumer who wants to halt or reverse hair loss, or at least maintain the thickness of hair associated with more youthful times, should be free from negative attributes and be otherwise convenient and easy to use, so that long term treatment can be tolerated. While assessing the suitability of employing for this purpose a glycosaminoglycanase inhibitor, such as those proposed by Unilever, we have found that problems can arise due at least in part to the natural stickiness that some of these sugar-like molecules exhibit. It is also apparent that hair treated with these molecules can become unnaturally stiff and, as a consequence the consumer may be dissuaded from continuing treatment.

We have discovered that this undesirable stickiness and hair stiffness is at least partly due to the presence of an excessive degree of hydrogen bonding in the glycosaminoglycanase inhibitor molecule, and we have now succeeded in disrupting at least some of the hydrogen bonding by employing in the composition a specific diol for this purpose, so as to at least diminish the severity of these undesirable attributes to acceptable levels.

DEFINITION OF THE INVENTION

Accordingly, the invention provides a composition for topical application to mammalian skin or hair, which comprises:

i) an effective amount of from 0.5 to 50% by weight of a glycosaminoglycanase inhibitor chosen from monosaccharide derivatives having the structure (1):

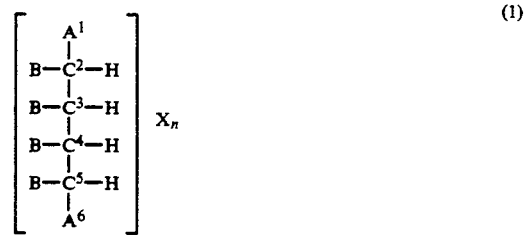

where
$A^1$ and $A^6$ are each chosen from

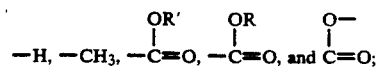

B is OR" or a lactone linkage to position 1 or 6, or —NHCOCH$_3$ and where

R is —H or C$_{1\text{-}20}$ alkyl,

R' is the remainder of the molecule joined through another C atom at positions 2 to 5 to form a lactone, R" is —H, C$_{1\text{-}20}$ alkyl or C$_{2\text{-}20}$ acyl; the group OR* being of either configuration with respect to the backbone of this structure;

X is chosen from H$^+$, alkali metal, especially sodium and potassium, alkaline earth metal, especially calcium and zinc, ammonium and alkanolammonium, especially ethanolammonium;

n is 0, or integer 1 or 2.

ii) from 0.5 to 50% by weight of ethane diol; and iii) up to 99% by weight of a cosmetically acceptable vehicle for the glycosaminoglycanase inhibitor.

DISCLOSURE OF THE INVENTION

The invention is concerned with a topical composition which comprises a glycosaminoglycanase inhibitor, whose function is to influence positively the growth, appearance and feel of the hair on the human scalp, but which possesses none of the undesirable in use stickiness reported by consumers applying such inhibitors topically and attributed to the sugar-like nature of the inhibitor molecule. Avoidance of this stickiness attribute has been achieved by including ethane diol in the composition.

The Glycosaminoglycanase Inhibitor

According to the invention, the composition comprises a glycosaminoglycanase inhibitor chosen from monosaccaride derivatives having the structure (1), as hereindefined. Suitable inhibitors which fit this general structure are exemplified below.

Aldonolactones

Examples of glycosaminoglycanase inhibitors having the structure (1) which are aldonolactones, are:

| | |
|---|---|
| L-Galactono-1,4-lactone, | (5) |
| L-Arabino-1,5-lactone, | (6) |
| D-Fucono-1,5-lactone, | (7) |
| D-Glucaro-1,4-lactone, | (8) |
| D-Glucaro-6,3-lactone | (9) |
| D-Glucurono-6,3-lactone, | (10) |
| Galactaric acid lactone, | (11) |
| 2-Acetamido-2-deoxygluconolactone, | (12) |
| 2-Acetamido-2-deoxygalactonolactone, | (13) |
| D-Glucaro-1,4:6,3-dilactone, | (14) |
| L-Idaro-1,4-lactone, | (15) |
| 2,3,5-Tri-O-acetyl-D-glucaro-1,4-lactone, | (16) and |
| 2,5-Di-O-acetyl-D-glucaro-1,4:6,3-dilactone. | (17) |

A particularly preferred inhibitor is D-Glucaro-1,4-lactone.

Hexosaccharic Acids

Examples of glycosaminoglycanase inhibitors having the structure (1) which are hexosaccharic acids are:

| | |
|---|---|
| Allosaccharic acid, | (18) |
| Altrosaccharic acid, | (19) |
| Glucosaccharic acid, | (20) |
| Mannosaccharic acid, | (21) |
| Gulosaccharic acid, | (22) |
| Idosaccharic acid, | (23) |
| Galactosaccharic acid, | (24) and |
| Talosaccharic acid. | (25) |

The hexosaccharic acids are preferably used as the corresponding disodium salt, and a particularly preferred example of which is glucarosaccharic acid, disodium salt.

The composition can comprise two or more glycosaminoglycanase inhibitors as herein defined. A particularly preferred mixture is D-glucaro-1,4-lactone, D-glucaro-6,3-lactone and glucarosaccharic acid, disodium salt.

The total amount of the glycosaminoglycanase inhibitor present in the composition according to the invention is from 0.5 to 50%, preferably from 1 to 20% and ideally from 2 to 10% by weight. The amount chosen should be an effective amount, that is sufficient to promote or maintain hair growth following topical application to the hair or skin, especially the scalp. It is to be understood that some inhibitors are more effective than others in this respect, in which case the dose of the glycosaminoglycanase inhibitor can be adjusted to suit its potency.

Ethane Diol

The composition according to the invention also comprises an effective amount of ethane diol, the function of which is to reduce excessive hydrogen bonding which can with some of the glycosaminoglycanase inhibitors lead to the composition being undesirably sticky in character, or the hair unnaturally stiff after treatment in view of their similarity to sugar molecules. Stickiness and/or stiffness resulting from use of the composition can thereby be reduced or eliminated.

Evidence will be provided later in the specification to show that compositions containing a glycosaminoglycanase inhibitor, as herein defined, are less sticky in use or the hair is less stiff when ethane diol is present in the composition, than when this diol is absent. By comparison, evidence will also be given to show that other diols are less effective in this respect.

The total amount of ethane diol present in the composition according to the invention is from 0.5 to 50%, preferably from 2 to 40% and ideally 5 to 20% by weight. The effective amount of ethane diol chosen should in any case be sufficient to reduce the inherent in-use stickiness of or stiffness due to the inhibitor which the ethane diol is intended to alleviate. It is accordingly apparent that when less than 0.5% ethane diol is present in the composition, there is likely to be little or no improvement in these negative attributes for which the inhibitor is responsible. Also, when the amount of ethane diol exceeds 50% by weight of the composition, further enhancement of the desirable sensory properties is unlikely to be noticeable to the user.

The Vehicle

The composition according to the invention also usually comprises a solid, semi-solid or liquid cosmetically and/or physiologically acceptable vehicle, to enable the glycosaminoglycanase inhibitor to be conveyed to the skin at an appropriate concentration. The nature of the vehicle will depend upon the method chosen for topical administration of the composition. The vehicle can itself be inert or it can possess cosmetic or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the inhibitor which therefore ensure that they can be applied to and distributed evenly over the hair and/or scalp at an appropriate concentration. The vehicle is preferably one which can aid penetration of the inhibitors into the skin to reach the immediate environment of the hair bulb. Compositions according to this invention can include water as a vehicle, and/or at least one cosmetically acceptable vehicle other than water.

Vehicles other than water than can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrogen, nitrous oxide;

Solvents, such as ethyl alcohol, methylene chloride, isopropanol, ethylene glycol monoethyl ether, diethylene glycol monobutyl ether, diethylene glycol monoethyl ether, dimethyl sulphoxide, dimethyl formamide, tetrahydrofuran;

Humectants, such as glycerine, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate, ethylene glycol distearate.

The amount of vehicle in the composition, including water if present, should preferably be sufficient to carry at least a portion of a selected glycosaminoglycanase inhibitor through the skin in an amount which is sufficient effectively to enhance hair growth. The amount of the vehicle can comprise the balance of the composition, particularly where no other ingredients are present in the composition. Accordingly, the vehicle or vehicles can comprise from 1 to 99%, preferably from 50 to 95% and ideally from 70 to 90% by weight of the composition.

Perfume

The composition according to the invention can also optionally comprise a perfume in an amount sufficient to make the composition acceptable to the consumer and pleasant to use. Usually, the perfume if present will form from 0.01 to 10% by weight of the composition.

Activity Enhancer

The composition according to the invention can also optionally comprise an activity enhancer.

The activity enhancer can be chosen from a wide variety of molecules that can function in different ways to enhance the hair growth effects of the glycosaminoglycanase inhibitor.

Some activity enhancers can also function as vehicles for the inhibitor.

Examples of activity enhancers include:

(a) Other Hair Growth Stimulants, such as:

i) Nicotinic acid and esters thereof, particularly benzyl, nicotinate, methyl nicotinate and ethyl nicotinate, ii) Panthenol iii) α-1,4 esterified disaccharides as described by Choay S.A. in EP-A-0 064 012, iv) Oligosaccharide deriviatives, as described by Unilever in EP-A-0 211 610, v) Minoxidil glucuronides, as described by Unilever in EP-A-0 242 967, vi) Minoxidil sulphates, as described by The Upjohn Co. in WO-A-86/04231, vii) Minoxidil, and other derivatives thereof as described by The Upjohn Co, in U.S. Pat. No. 4,139,619.

Particularly preferred mixtures of minoxidil and a glycosaminoglycanase inhibitor according to the invention include the following:

Minoxidil and D-glucaro-6,3-lactone,
Minoxidil and D-glucaro-1,4-lactone, and
Minoxidil and glucosaccharic acid, disodium salt.

viii) Proteoglycanase inhibitors, glycosaminoglycan chain cellular uptake inhibitors and glycosaminoglycanase inhibitor other than those disclosed herein, as described by Unilever in EP-A-0 277 428, ix) Ethylenediaminetetraacetic acid or salts thereof, as described by Redken Laboratories, Inc. in U.S. Pat. No. 4,814,351, x) Esters of pyroglutamic acid, as described by Lever Brothers Company in U.S. Pat. No. 4,774,255, especially:

pyroglutamic acid n-hexyl ester,
pyroglutamic acid n-octyl ester,
ethyl-2-[pyroglutamoyloxy]-n-propionate,
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

xi) Aryl-substituted ethylenes, as described by Unilever in EP-A-0 403 238, xii) Mono N-acylated amino acids, as described by Unilever in EP-A-0 415 598, especially:

N-acetyl glycine

Xiii) Saturated or unsaturated aliphatic alcohols having an odd number of carbon atoms of from 3 to 25 in number, especially:

n-nonyl alcohol xiv) Saturated or unsaturated aliphatic carboxylic acids having an odd number of carbon atoms of from 3 to 25 in number, especially:

nonanoic acid (b) Penetration Enhancers:

The composition according to the invention can also optionally comprise one or more penetration enhancers, which can potentiate the benefit of the glycosaminoglycanase inhibitor by improving its delivery through the stratum corneum to its site of action in the immediate environment of the hair follicle close to the hair bulb.

Examples of penetration enhancers include:

Propan-2-ol
Propan-1-ol
Propan-1,2-diol
Butan-1,4-diol
Dibutyl sebacate
Dibutyl phthalate
2-hydroxypropanoic acid 2-hyroxyoctanoic acid, and 1-alkyl (C6-18) derivatives of azacycloheptan-2-one, such as 1-Dodecylazacycloheptan-2-one.

Further examples of penetration enhancers include surface active agents.

(c) cationic polymers chosen from:
Guar Hydroxypropyltrimonium chloride
Quaternium-19
Quaternium-23
Quaternium-40
Quaternium-57
Poly(dipropyldiallylammonium chloride)
Poly(methyl-β-propaniodiallylammonium chloride)
Poly(diallylpiperidinium chloride)
Poly(vinyl pyridinium chloride)
Quaternised poly (vinyl alcohol)
Quaternised poly(dimethylaminoethylmethacrylate); and
mixtures thereof The amount of activity enhancer, when employed in accordance with the invention, will normally be from 0.1 to 50%, preferably from 0.5 to 25% and most preferably from 0.5 to 10% by weight of the composition.

Water-Soluble Silicones

The composition according to the invention can also optionally comprise an effective amount of one or more water-soluble or water-dispersible silicones, whose presence is further to reduce the undesirable gritty or sticky feel that the glycosaminoglycanase inhibitor can impart to the hair following topical application of the composition.

Preferred examples of water-soluble ethoxylated silicones are:
Dimethicone copolyol, available from Dow Corning as DC190 and DC192.

The amount of water-soluble silicone, when employed in accordance with the invention, will normally be from 0.01 to 10%, preferably from 0.05 to 2% by weight.

Thickening Agents

The composition according to the invention can also optionally comprise an effective amount of one or more thickening agents.

Preferred thickening agents are:
gums, such as
 xanthan gum
 guar gum
 locust bean gum
 Biopolymer PS 87
modified cellulose, such as
 sodium carboxymethyl cellulose
 hydroxypropyl cellulose
 methyl cellulose
acrylic polymers, such as
 carboxyvinyl polymer
clays, such as
 hectorites
 bentonites

Other Glycosaminoglycanase Inhibitor Adjuncts

The composition according to the invention can also, optionally contain adjuncts other than those already mentioned, depending on the form of the intended product. It is, for example, possible to include anti-danduff agents, such as Octopirox, antiseptics, preservatives, antioxidants such as sodium metabisulphite, emulsifiers and colouring agents, which can improve the stability and consumer appeal of the composition.

The composition according to the invention can also be employed as a vehicle for a wide variety of cosmetically or pharmaceutically active ingredients, particularly ingredients which have some beneficial effect other than the promotion or maintenance of hair growth when applied to the skin.

Preservation of the Composition

The composition according to the invention is preferably preserved in such a manner that it will enjoy an extended shelf life following manufacture and prior to sale and use. Ideally the composition will have an indefinite shelf life.

It is apparent that the glycosaminoglycanase inhibitor is likely to be prone to attack by bacteria, moulds and fungi and other microbial influences, particularly at pH values near that of the skin that characterise the preferred composition. The shelf-life of the composition can therefore be unacceptably short due to the biodegradation of the inhibitor unless steps are taken to preserve the composition.

In order to be preserved, the composition should preferably be free, or substantially free, from viable microbial contaminants that are capable of resulting in microbial spoilage of the composition, and/or biodegradation of the inhibitor prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of the methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Use of Chemical Preservatives

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iii) Water Activity Depressants

The composition according to the invention can also be preserved by the inclusion of a water activity depressant such as glycerol, propylene glycol, sorbitol, sugars and salts, for examples alkali metal halides sulphates and carboxylates. When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, moulds and fungi will not proliferate.

Process

The invention provides a process for the preparation of a composition suitable for topical application to mammalian skin or hair which comprises mixing a glycosaminoglycanase inhibitor as herein defined, with ethane diol and a suitable vehicle to provide a composition according to the invention, in which the inhibitor forms from 0.5 to 50% by weight of the composition.

Product Form and Container

The composition of the invention can be formulated as liquids, for example as a lotion, shampoo, conditioner, milk or cream for use in conjunction with an applicator such as roll-ball applicator, or a spray device such as an aerosol can containing propellant, or a container fitted with a pump to disperse the liquid product. Alternatively, the compositions of the invention can be solid or semi-solid, for example as a stick, cream or gel, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Glycosaminoglycanase Inhibitor for Inducing Maintaining or Increasing Hair Growth The invention also provides for the use of the glycosaminoglycanase inhibitor as herein defined, together with ethane diol, for topical application to mammalian skin or hair for inducing, maintaining or increasing hair growth.

The composition according to the invention is primarily intended for topical application to the scalp of the human subject, particularly where the head is already bald or balding, in order the promote the regrowth of terminal hair, and/or to maintain hair thickness on thinning sites. The composition can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5 g daily containing from 0.00001 to 1 g of a selected glycosaminoglycanase inhibitor over the period of at least six months will in most cases result in an improvement in hair growth, or in reducing hair loss.

Evidence of Demonstrate Delivery to the Hair Bulb of the Glycosaminoglycanase Inhibitor It is believed that the intact glycosaminoglycan fragment of proteoglycan is vital to the growth of new hair, or the continued growth of the existing hair, and that certain enzymes, known as glycosaminoglycanases, which occur in the region of the hair bulb are implicated in the degradation of the glycosaminoglycan which in turn leads to cessation of hair growth.

Accordingly, introduction of inhibitors of glycosaminoglycanase into the immediate environment of the hair bulb will reduce or prevent glycosaminoglycan degradation and so permit hair growth to continue. Particularly preferred examples of glycosaminoglycanase inhibitors are the families of aldonomonolactones and hexosaccharic acids referred to herein.

For inhibitors such as these to be effective, when applied topically to the skin or hair, it is necessary for them to penetrate through the skin to reach the immediate environment of the hair bulb, and experiments using radio labelled glucarolactone, as an example of the glycosaminoglycanase inhibitor, to demonstrate this are now described.

Methodology

In order to simulate human skin penetration in vivo, full thickness pig skin was used in a flow-through skin penetration cell system. For this purpose, the technique described by Bronough R L, and Stuart R F in "Methods for in vitro percutaneous absorption studies IV: The flow-through diffusion cell", published in J. Pharm. Sci. 74 (1985) 164-167 was used.

This system allows for the study of percutaneous absorption from topically applied substances in a controlled manner, i.e. at controlled temperature and with constant receptor fluid flow rate. The flow-through skin penetration cell has a surface area of skin of 0.38 $cm^2$ exposed to a formulation containing a test substance. At time zero, 25 $\mu$l of a formulation containing tracer amounts of $^{14}$C-labelled glucarolactone was applied to the skin and left for 20 hours. During this period of penetration, receptor fluid flowing underneath the dermal side of the skin was collected in fractions at 2 hour intervals. At time 20 hours, the skin was vigorously washed to remove all non-absorbed material, the remaining receptor fluid in the cell also being collected at this time.

Subsequently, the piece of skin was detached from the cell and keratatomed at a thickness of about 1.3 mm. This procedure will separate the lower section of the dermis from that containing the stratum corneum, viable epidermis, upper part of dermis and neck of hair follicle. To refine further the picture of distribution of radioactivity, the upper section was subsequently tape stripped 5 times using transparent adhesive tape to remove residual radioactive materials adhering to the outer surface of the skin. All these sections were digested and counted for radioactivity. Each penetration cell therefore yielded 4 results:

i) transdermal penetration, i.e. the amount retrieved in receptor fluid flowing on the dermal side of the skin;

ii) tape strips, i.e. amounts of radio active material adhering to the skin surface;

iii) upper section of skin, i.e. remainder of stratum corneum, neck of hair follicle, viable epidermis and upper part of dermis;

iv) lower section of skin, i.e. remainder of dermis containing the remaining part of hair follicles and dermal papillae.

The results obtained from categories ii), iii) and iv) above together constitute the amounts retrieved from within the skin, i.e. dermal penetration. The results may be expressed as percentage of dose applied, or as the actual amounts delivered.

Formulation Tested

The following formulation was used to determine penetration and delivery of glucarolactone in accordance with the Bronaugh flow-through skin penetration cell technique:

| Ingredients | % w/w |
|---|---|
| Glucarolactone | 8 |
| Ethanol | 10 |
| Xanthan gum | 0.3 |
| Ethane diol | 10 |
| Dimethicone copolyol | 1 |
| Octopirox | 0.1 |
| Na-metabisulphite | 0.15 |
| Minor ingredients | q.s. |
| Water | to 100 |
| pH adjusted with NaOH to | 4.2 |

Results

Scintillation counting was employed to determine the amount of the enzyme inhibitor, glucarolactone, which had penetrated the skin to a point where it would be available to inhibit glycosaminoglycanase in the immediate environment of the hair bulb.

The results obtained are shown in the following Table 1 in which the values given represent percentages of the glucarolactone dose applied topically which actually penetrates into and through the skin and is recovered at various levels. In addition, the actual amounts of penetrated glucarolactone is given. The results shown are the average and standard error of the mean of 33 determinations.

TABLE 1

Penetration of glucarolactone (GL) into and through skin expressed as percentage of the applied dose and amounts delivered ($\mu$g).

| Skin Section | Percentage of Applied Dose | Actual Amount GL Delivered ($\mu$g) |
|---|---|---|
| Transdermal | 0.398 ± 0.126 | 7.80 ± 2.47 |
| Dermal | 3.719 ± 0.848 | 72.87 ± 16.62 |
| tapes | 0.122 ± 0.020 | 2.38 ± 0.39 |
| upper section | 0.707 ± 0.153 | 13.86 ± 3.00 |
| lower section | 2.890 ± 0.731 | 56.63 ± 14.33 |
| Total | 4.117 | 80.67 |

Conclusions

It can be concluded from these results that penetration through the skin of glucarolactone is of the order of from 2 to 4% after 20 hours. However, bearing in mind the high intrinsic activity of this inhibitor, it is apparent that the local concentration in the immediate environment of the hair bulb will be sufficiently high to inhibit glycosaminoglycanase. Hence, it can be concluded that topical application of glucarolactone, particularly from a composition in accordance with the invention, is sufficient positively to influence hair growth.

Evidence to Demonstrate the Role of Ethane Diol in Alleviating the Inherent Stickiness and Hair Stiffness of the Composition Due to the Presence of the Sugar-Like Glycosaminoglycanase Inhibitor Two subjective methods, each involving a panel of volunteers, were employed to evaluate the sensory benefits achieved when ethane diol is employed in the composition to reduce or eliminate the sensory negative attributes associated with the use of the glycosaminoglycanase inhibitor. In addition, a objective method was used to determine the hair stiffness of a composition according to the invention and of conventional compositions.

1. SUBJECTIVE MEASUREMENT OF STICKINESS

Method

This method uses line scaling as a tool for panelist estimation. A straight line one meter in length was drawn on a bench surface. One end of this line was labelled "no stickiness" and the other end was labelled "extremely sticky".

Each panellist received 0.5 ml of a test formulation dosed onto the forearm and instructed to massage it into the skin. The evaporation rate was increased by the use of a hair drier. The panellist was instructed to assess the product for stickiness and to indicate the amount of stickiness by placing a mark on the one meter line.

The test area of the forearm was washed and dried and the procedure repeated using other test products. The distance of each mark was then measured along the line from the end representing no stickiness.

This test was repeated with five panellists and the score for each formulation was then averaged. A low score indicated a less sticky product.

Results

All formulations contained, by weight, 8% glucarolactone and 20% ethanol.

The mean stickiness results were as follows:

| Additions | Mean Stickiness |
|---|---|
| No additions | 455 |
| 25% Propylene Glycol + 0.5% Xanthan Gum | 164 |
| 25% Ethane Diol + 0.5% Xanthan Gum | 107 |

Conclusions

It can be concluded from these results that ethane diol is significantly superior to propylene glycol in reducing the subjective stickiness due to glucarolactone.

2. SUBJECTIVE ASSESSMENT OF HAIR STIFFNESS

Method

In accordance with this method, ten panellist were asked to compare the properties of products comprising glucarolactone by applying these products to hair switches and commenting on the resultant feel. Finally, pretreated and dried switches were examined, both with and without combing.

Results

The products tested contained, by weight, 8% glucarolactone, 20% ethanol, 0.5% xanthan gum, other minor ingredients including perfume, and 25% propylene glycol or ethane diol.

The propylene glycol-containing product was perceived as being very sticky when applied to the hair switch and then dried. These hair switches were perceived as being extensively matted.

The ethane diol-containing product was perceived to have less of these problems inasmuch as the hair switches were less sticky and not extensively matted.

Conclusions

It can be concluded from these observations that ethane diol is significantly superior to propylene glycol in reducing the subjective hair stiffness due to glucarolactone.

3. OBJECTIVE MEASUREMENT OF HAIR STIFFNESS

Method

In this method the one end of an exactly vertically hanging hair switch treated with the respective test composition was fixed with a clamp attached to a goniometer. The freely hanging switch was rotated through a predetermined angle in a vertical plane about a horizontal axis, were the vertical plane ran through the hair switch and the horizontal axis ran through the clamped end of the hair switch. The resulting horizontal displacement of the free end of the hair switch was recorded by lining up a sliding pointer attached to a scale graduated in centimeters with the suitably labelled centre of the free end of the hair switch. The exactly vertical position of the hair switch was accorded an angle of 0° and a displacement of the free end of 0 cm.

Beginning at +45° the clamp was rotated in steps of 5° through the verticle plain to −45° and back to +45°. The resulting displacement of the free end of the hair switch was recorded for any angle to give a value $d_\alpha$ where $\alpha$ is the angle of rotation. As a measure of stiffness of the hair switch tested the shear stiffness (SS) was computed according to the following equation:

$$SS(cm/degree) = (d_{+45°} - d_{-45°})/90$$

Moreover, the shear stiffness (SS) obtained by using the test solutions was compared with the shear stiffness of an untreated control switch to give the % change in shear stiffness according to the following equation:

$$\% \text{ change in } SS = (SS_{test} - SS_{control})/SS_{control} \times 100$$

Treatment of the Hair Switches

The hair switches tested where 2 cm wide, 20 cm long and base washed using a non-depositing shampoo before drying at 50° C. for one hour. The respective test composition was applied to the dried switch using 0.5 ml of the composition for each side of the switch. The switch was then dried again at 50° C. for one hour. Subsequently, the switch was equilibrated at 21° C. and 50% relative humidity for one hour. The one end of the hair switch was then fixed to the goniometer and the position of the switch was adjusted so that the free length of the hair was 19 cm. The hair switch was combed to reduce any high initial stiffness. Subsequently the clamp of the goniometer was rotated to give values for the horizontal displacement of the free end of the hair switch as described above.

Results

All test compositions contained, by weight, 8.0% glucarolactone, 10% ethanol and 0.3% xanthan gum.

The shear stiffness values, expressed as cm/degree, were as follows:

| Additions | Shear Stiffnes (cm/degree) |
|---|---|
| — | 0.258 |
| 10% glycerol | 0.156 |
| 10% propylene glycol | 0.150 |
| 10% ethane diol | 0.109 |

The shear stiffness of an untreated control switch was 0.068 cm/degree.

Accordingly, the % changes in shear stiffness were as follows:

| Additions | % change in shear stiffness |
|---|---|
| — | 279.4 |
| 10% glycerol | 128.8 |
| 10% propylene glycol | 120.6 |
| 10% ethane diol | 60.3 |

These results illustrate the superiority of compositions including ethane diol to conventional compositions in reducing the hair stiffness due to glucaro lactone.

EXAMPLES

The invention is illustrated by the following example formulations, each of which includes at least one glycaroaminoglycanase inhibitor, which is identified by the structure number designated to it hereinbefore.

EXAMPLE 1

This Example illustrates a lotion according to the invention which is suitable for topical application to the scalp in order to promote hair growth.

The lotion has the following formulation:

| | % w/w |
|---|---|
| Inhibitor (5) | 5 |
| Ethane diol | 10 |
| Perfume | q.s. |
| Ethanol | to 100 |

EXAMPLE 2

This Example illustrates a hair tonic which is suitable for application to hair or scalp.

The hair tonic has the following formulation:

| | % w/w |
|---|---|
| Inhibitor (6) | 8 |
| Ethane diol | 15 |
| Water | 49 |
| Perfume | q.s. |
| Ethanol | to 100 |

EXAMPLE 3

This Example also illustrates a lotion which is suitable for topical application to the scalp.

The lotion has the following formulation:

| | % w/w |
|---|---|
| Inhibitor (7) | 10 |
| Ethane diol | 10 |
| Propan-2-ol | 10 |
| Perfume | q.s. |
| Ethanol | to 100 |

EXAMPLE 4

This Example also illustrates a hair tonic which is suitable for application to hair or scalp.
The hair tonic has the following formulation:

|  | % w/w |
|---|---|
| Inhibitor (8) | 6 |
| Ethane diol | 12 |
| Ethanol | 40 |
| Perfume | q.s. |
| Water | to 100 |

EXAMPLES 5 TO 8

The following formulations represent lotions which can be used topically in the treatment of bald or balding male or female heads.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Ethane diol | 10 | 10 | 10 | 10 |
| Inhibitor (9) | 10 | — | — | — |
| Inhibitor (10) | — | 5 | — | — |
| Inhibitor (11) | — | — | 8 | — |
| Inhibitor (12) | — | — | — | 6 |
| Perfume | 1 | 1 | 1 | 1 |
| Water | to 100 | 100 | 100 | 100 |

EXAMPLES 9 TO 12

The following formulations represent creams which can be used in the treatment of baldness.

|  | % w/w | | | |
|---|---|---|---|---|
|  | 9 | 10 | 11 | 12 |
| Cetyl alcohol polyoxyethylene (13) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acid | — | — | — | 4 |
| Ethane diol | 10 | 10 | 10 | 10 |
| Inhibitor (13) | 2 | — | — | — |
| Inhibitor (14) | — | 5 | — | — |
| Inhibitor (15) | — | — | 7 | — |
| Inhibitor (16) | — | — | — | 9 |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water | to 100 | 100 | 100 | 100 |

EXAMPLE 13

This Example illustrates a water-in-oil high internal phase emulsion containing ester according to the invention The emulsion consisted of 10% by volume oily phase and 90% by volume aqueous phase.
The oily phase and the aqueous phase had the following constitution:

|  | % w/w |
|---|---|
| Oily phase | |
| Sorbitan monooleate | 20 |
| Quaternium-18 hectorite | 5 |
| Liquid paraffin | 75 |
| Aqueous phase | |
| Inhibitor (17) | 5 |
| Ethane diol | 5 |
| Xanthan gum | 1 |
| Preservative | q.s. |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following Examples 14 and 15 illustrate shampoos for use in washing the hair and scalp, and for promoting hair growth on the scalp.

EXAMPLE 14

|  | % w/w |
|---|---|
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS O3D) | 1 |
| Polyglycol-polyamine condensation resin (POLYQUART H) [50% active) | 1.5 |
| Preservative, colouring matter, salt | 0.58 |
| Ethane diol | 15 |
| Inhibitor (18) | 5 |
| Perfume | q.s. |
| Water | to 100 |

EXAMPLE 15

|  | % w/w |
|---|---|
| Sodium lauryl ether sulphate (2 EO) [100% AD] | 12 |
| POLYMER JR400 | 2.5 |
| BRIPHOS O3D | 2.5 |
| Ethane diol | 20 |
| Inhibitor (19) | 4 |
| Magnesium Sulphate | 5 |
| Perfume | q.s. |
| Water | to 100 |

EXAMPLE 16

This Example also illustrates a lotion which is suitable for topical application to the scalp.
The lotion has the following formulation:

|  | % w/w |
|---|---|
| Inhibitor (20) [as disodium salt] | 8 |
| Ethane diol | 12 |
| Propan-2-ol | 10 |
| Perfume | q.s. |
| Ethanol | to 100 |

EXAMPLE 17

This Example also illustrates a hair tonic which is suitable for application to hair or scalp.
The hair tonic has the following formulation:

|  | % w/w |
| --- | --- |
| Inhibitor (21) | 10 |
| Ethane diol | 14 |
| Ethanol | 40 |
| Perfume | q.s. |
| Water | to 100 |

The following examples 18 to 20 illustrate shampoos for use in washing the hair and scalp, and for promoting hair growth on the scalp.

EXAMPLE 18

|  | % w/w |
| --- | --- |
| Monoethanolamine lauryl sulphate: [100% AD] | 20 |
| Guar Hydroxypropyltrimonium chloride | 3 |
| Phosphate ester surfactant | 1.7 |
| Coconut diethanolamide | 5 |
| Ethane diol | 8 |
| Inhibitor (22) | 10 |
| Zinc gluconate | 3 |
| Perfume | q.s. |
| Water | to 100 |
| pH adjusted to | 6.5 |

EXAMPLE 19

|  | % w/w |
| --- | --- |
| Sodium lauryl ether sulphate (3 EO): [100% AD] | 12 |
| JAGUAR C13S | 0.3 |
| BRIPHOS O3D | 1 |
| Ethane diol | 10 |
| Inhibitor (23) | 12 |
| Sodium chloride | 4 |
| Perfume | q.s. |
| Water | to 100 |
| pH adjusted to | 6.5 |

EXAMPLE 20

|  | % w/w |
| --- | --- |
| Sodium lauryl ether sulphate (2 EO) [100% AD] | 12 |
| POLYMER JR400 | 3 |
| BRIPHOS O3D | 1 |
| Opacifier | 9 |
| Ethane diol | 9 |
| Inhibitor (24) | 5 |
| Perfume | q.s. |
| Water | to 100 |
| pH adjusted to | 6.5 |

EXAMPLES 21

This Example illustrates a powder composition according to the invention which can be applied topically to the scalp.

|  | % w/w |
| --- | --- |
| Chemically modified starch | 5 |
| Boric acid | 10 |
| Zinc oxide | 5 |
| Ethane diol | 10 |
| Inhibitor (25) | 8 |
| Minoxidil glucuronide | 5 |
| Perfume | q.s. |
| Chalk | 10 |
| Talc | to 100 |

EXAMPLE 22

The following example illustrates a lotion according to the invention which can be applied topically to the scalp to prevent hair loss and stimulate hair growth.

|  | % w/w |
| --- | --- |
| Inhibitor (8) | 7 |
| Minoxidil | 0.2 |
| Ethane diol | 10 |
| Ethanol | 16 |
| Citric acid | 1.05 |
| Water | to 100 |
| pH adjusted to 4.2 with sodium hydroxide | |

EXAMPLES 23 & 24

These examples illustrate hair tonics which are suitable for application to the hair and scalp.
The hair tonics had the following formulation:

|  | % w/w | |
| --- | --- | --- |
|  | 23 | 24 |
| Inhibitor (7) | 6 | — |
| Inhibitor (8) | — | 8 |
| Ethane diol | 12 | 14 |
| Ethanol | 50 | 50 |
| Perfume | q.s. | q.s. |
| Water | to 100 | to 100 |

EXAMPLE 25

This example illustrates a microgel which is suitable for topical application to hair or scalp.
The gel had the following formulation

|  |  | % w/w |
| --- | --- | --- |
| A. | Polyoxyethylene (10) oleyl ether | 14.5 |
|  | Polyoxyethylene fatty glyceride | 14.5 |
|  | Light liquid petroleum | 13.7 |
|  | Propylene glycol | 7.6 |
|  | Sorbitol | 5.9 |
|  | Ethane diol | 10 |
|  | Inhibitor (8) | 6 |
|  | Inhibitor (9) | 8 |
|  | Inhibitor (20) [as disodium salt] | 4 |
| B. | Perfume | q.s. |
| C. | Water | to 100 |

The microgel was prepared by heating part A to 90° C. and part C to 95° C. and then adding part C to part A with stirring. Part B was then added at 70° C. and the final mixture cooled and poured into jars at 55° C. to 60° C. On further cooling, a gel was formed.

EXAMPLE 26

This example illustrates a shampoo which is suitable for topical application to hair in order to cleanse it, at the same time delivering a hair growth promoter to the scalp to enhance hair growth or regrowth.

The shampoo had the following formulation:

|  | % w/w |
|---|---|
| Triethanolamine lauryl sulphate | 16.8 |
| Coconut diethanolamide | 3.0 |
| Hydroxypropylmethyl-cellulose (1) | 0.25 |
| Corn syrup (80% solids) (2) | 20.5 |
| Dimethylpolysiloxane (3) | 1.0 |
| Cationic cellulose (4) | 0.5 |
| Ethyl alcohol (SDA 40) | 9.0 |
| Vinyl carboxy polymer (5) | 0.75 |
| Ethane diol | 10 |
| Inhibitor (10) | 10 |
| Perfume, colour, preservative | q.s. |
| Water | to 100 |
| Acid or base to pH: | 6.5 |

(1) Methocel E4M (Dow Chemical)
(2) 42 Dextrose equivalent (Staley 1300)
(3) 60,000 centistokes (Viscasil, GEC)
(4) Polymer JR 400
(5) Carbopol 941 (BF Goodrich)

EXAMPLES 27 TO 28

The following formulations represent lotions which can be used topically in the treatment of bald or balding male or female heads.

|  | % w/w | |
|---|---|---|
|  | 27 | 28 |
| Hydroxyethyl cellulose | 0.4 | — |
| Absolute ethanol | 25 | 25 |
| Propane-1,2-diol | — | — |
| Butane-1,3-diol | 38.4 | 38.8 |
| Paramethyl benzoate | 0.2 | 0.2 |
| Inhibitor (19) [as disodium salt] | 5 | — |
| Inhibitor (8) | — | 8 |
| Perfume | 1 | 1 |
| Ethane diol | 4 | 10 |
| Water | to 100 | 100 |

EXAMPLE 29

The following formulation represents a hair growth tonic in accordance with the invention.

|  | % w/w |
|---|---|
| Xanthan gum (Kelzan) | 0.3 |
| Ethane diol | 10 |
| Ethanol | 10 |
| Dimethicone copolyol | 1 |
| Inhibitor (8) | 8 |
| Octopirox | 0.1 |
| Sodium metabisulphite | 0.15 |
| Minor ingredients | qs |
| Water | to 100 |
| Viscosity | 1000 mPa · s |

-continued

|  | % w/w |
|---|---|
| pH adjusted to | 4.2 |

We claim:
1. A composition for topical application to mammalian skin of hair, comprising:
   (i) from 0.5 to 50% by weight of a glycosaminoglycanase inhibitor selected from the group consisting of glucarolactone, glucosaccharic acid, salts of glucosaccharic acid and mixtures thereof;
   (ii) from 10 to 25% by weight of ethane diol; and
   (iii) up to 99% by weight of a cosmetically acceptable vehicle for the glycosaminoglycanase inhibitor.

2. A method for at least maintaining hair growth while avoiding stickiness and stiffness imparted by a glycosaminoglycanase inhibitor, the method comprising applying to the hair or skin a composition comprising:
   (i) from 0.5 to 50% by weight of a glycosaminoglycanase inhibitor selected from the group consisting of glucarolactone, glucosaccharic acid, salts of glucosaccharic acid and mixtures thereof;
   (ii) from 10 to 25% by weight of ethane diol; and
   (iii) up to 99% by weight of a cosmetically acceptable vehicle for the glycosaminoglycanase inhibitor.

3. A composition according to claim 1, in which the glycosaminoglycanase inhibitor is D-glucaro-1,4-lactone.

4. A composition according to claim 1, in which the glycosaminoglycanase inhibitor is D-glucaro-6,3-lactone.

5. A composition according to claim 1, in which the glycosaminoglycanase inhibitor is glucosaccharic acid.

6. A composition according to claim 1, in which the glycosaminoglycanase inhibitor comprises a mixture of D-glucaro-1,4-lactone, D-glucaro-6,3-lactone and the disodium salt of glucosaccharic acid.

7. A composition according to any one of claims 1 to 5, in which the glycosaminoglycanase inhibitor forms from 1 to 20% by weight.

8. A composition according to any one of claims 1 to 5, in which the ethane diol forms from 2 to 40% by weight.

9. A composition according to claim 1, which further comprises an activity enhancer selected from the group consisting of nicotinic acid or an ester thereof, minoxidil and silicone.

10. A composition according to claim 9, in which the activity enhancer is nicotinic acid or an ester thereof.

11. A composition according to claim 9, in which the activity enhancer is minoxidil.

12. A composition according to claim 1, which further comprises a silicone.

13. A composition according to claim 12, in which the silicone is dimethicone copolyol.

14. A composition according to claim 1, which further comprises a thickening agent.

15. A composition according to claim 14, in which the thickening agent is xanthan gum.

* * * * *